US 9,999,460 B2

(12) United States Patent
Shazly et al.

(10) Patent No.: US 9,999,460 B2
(45) Date of Patent: Jun. 19, 2018

(54) SURGICAL ROD BENDING

(71) Applicant: University of South Carolina, Columbia, SC (US)

(72) Inventors: Tarek Shazly, Columbia, SC (US); Jahid Ferdous, Columbia, SC (US); Gregory Grabowski, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days. days.

(21) Appl. No.: 14/940,818

(22) Filed: Nov. 13, 2015

(65) Prior Publication Data

US 2016/0263646 A1  Sep. 15, 2016

Related U.S. Application Data

(60) Provisional application No. 62/079,596, filed on Nov. 14, 2014.

(51) Int. Cl.
 *A61B 17/88* (2006.01)
 *B21D 7/02* (2006.01)
 *B21D 11/10* (2006.01)

(52) U.S. Cl.
 CPC .......... *A61B 17/8863* (2013.01); *B21D 7/02* (2013.01); *B21D 11/10* (2013.01)

(58) Field of Classification Search
 CPC ...... A61B 17/8863; B21D 7/02; B21D 7/022; B21D 7/025; B21D 7/028; B21D 7/04; B21D 7/08; B21D 7/10; B21D 7/12; B21D 5/14; B21D 11/10; B21D 43/006; B21D 43/02; B21D 43/021; B21D 43/026; B21D 43/028; B21D 43/04; B21D 43/105; B21D 43/13; B21D 43/28
 See application file for complete search history.

(56) References Cited

U.S. PATENT DOCUMENTS 4,061,005 A * 12/1977 Kawanami ............ B21D 7/025
  72/128
6,820,450 B2 * 11/2004 Yamada .................. B21D 7/12
  72/149

(Continued)

FOREIGN PATENT DOCUMENTS

DE      3044646 A1 *  9/1982 ............ B21D 7/022
WO  WO 2013085982 A2 *  6/2013 ............ B21D 7/022

OTHER PUBLICATIONS

EPO Machine Translation oF DE 3044646 A1.*

*Primary Examiner* — Shelley Self
*Assistant Examiner* — Pradeep C Battula
(74) *Attorney, Agent, or Firm* — Dority & Manning, P.A.

(57) ABSTRACT

A system for bending a surgical rod including a linear actuator and a rotational actuator is provided. The linear actuator is configured for moving the surgical rod along a linear direction of the system, and the rotational actuator is configured for rotating the surgical rod about the linear direction. A bending mechanism is also provided positioned downstream of the linear and rotational actuators configured for bending the surgical rod. A controller is operably connected to the linear and rotational actuators and the bending mechanism, the controller configured to activate the various components and bend the surgical rod into a desired three-dimensional shape.

9 Claims, 4 Drawing Sheets

(56) References Cited

U.S. PATENT DOCUMENTS

| | | | |
|---|---|---|---|
| 7,344,537 B1 * | 3/2008 | Mueller | A61B 17/7037 606/278 |
| 7,454,939 B2 * | 11/2008 | Garner | B21D 7/063 72/218 |
| 9,003,859 B2 * | 4/2015 | Paris | B21D 7/063 72/362 |
| 9,636,162 B2 * | 5/2017 | Crawford | B21D 7/022 |

* cited by examiner

SURGICAL ROD BENDING

PRIORITY CLAIM

The present application is a non-provisional patent application claiming the benefit of and priority to U.S. Provisional Patent Application No. 62/079,596, filed Nov. 14, 2014, which is incorporated herein by reference for all purposes

FIELD OF THE INVENTION

The present subject matter relates generally to a system and method for bending one or more surgical rods.

BACKGROUND OF THE INVENTION

With certain spinal conditions it is desirable or medically necessary to undergo surgery in order to correct and/or treat such conditions. For example, patients suffering from an idiopathic spinal deformity, degenerative spinal deformity, or certain spinal traumas may require surgery in order to obtain a desired quality of life.

One such surgery is referred to as a spinal fusion, wherein two or more vertebrae are joined. In some cases, spinal fusion surgery may be augmented by a process called fixation, wherein a plurality of pedicle screws may be attached to the vertebrae bilaterally along either side of the vertebrae. A surgical rod may be attached to the pedicle screws along either side of the vertebrae in order to stabilize the vertebrae and facilitate the fusion.

However, due to the contours of the vertebrae, each rod must be modified such that a shape of the rod corresponds to the positioning of the pedicle screws. Generally, in order to modify the shape of a rod, a surgeon or other professional will manually bend the rods in an iterative "trial and error" process. However, such a process, can be complicated, inaccurate, and overly time-consuming Notably, complications can arise with an increase in operative time. Additionally, as each rod undergoes iterative manual manipulations, certain material properties of the rods, e.g., strength, may be detrimentally affected. Further, inaccurately shaped rods may place additional or unnecessary stress on the pedicle screws, as well as the vertebrae, which may lead to, e.g., premature loosening of such pedicle screws.

Accordingly, a system for more quickly and accurately bending a surgical rod would be useful. Moreover, a method for quickly and accurately bending a surgical rod would be particularly beneficial.

BRIEF DESCRIPTION OF THE INVENTION

Aspects and advantages of the invention are set forth below in the following description, or may be obvious from the description, or may be learned through practice of the invention.

In one exemplary embodiment of the present disclosure, a system for bending a surgical rod is provided. The system defines a linear direction and includes a linear actuator configured for moving a surgical rod along the linear direction and a rotational actuator configured for rotating the surgical rod about the linear direction. The system also includes a bending mechanism configured for bending the surgical rod and a controller. The controller is operably connected to the linear actuator, the rotational actuator, and the bending mechanism. The controller is configured to activate the linear actuator, the rotational actuator, and the bending mechanism to bend the surgical rod into a desired three dimensional shape.

In one exemplary aspect of the present disclosure a method for bending a surgical rod is provided. The method includes receiving with a controller information indicative of a desired shape for a surgical rod and determining a first bend location of the surgical rod. The method also includes moving the surgical rod along a linear direction with a linear actuator such that the first bend location of the surgical rod is positioned in a bending mechanism. Additionally, the method includes bending the surgical rod at the first bend location a determined amount using the bending mechanism.

These and other features, aspects and advantages of the present disclosure will become better understood with reference to the following description and appended claims. The accompanying drawings, which are incorporated in and constitute a part of this specification, illustrate embodiments of the disclosure and, together with the description, serve to explain the principles of the disclosure.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

DETAILED DESCRIPTION OF THE INVENTION

Figure 1:
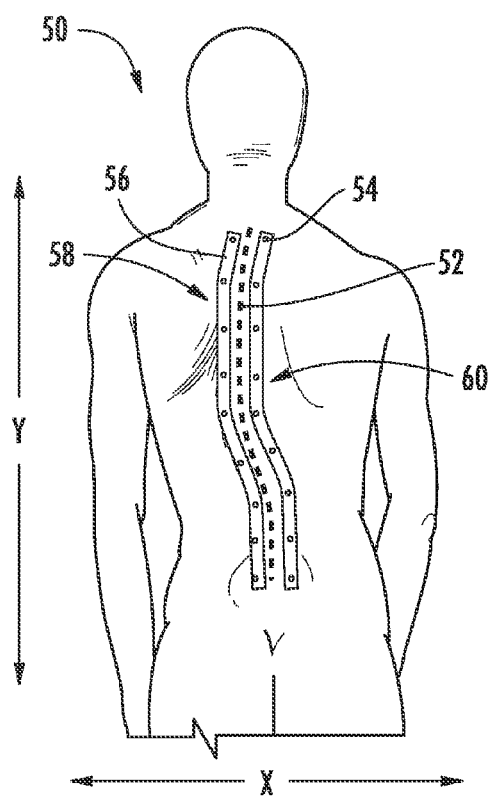
FIG. 1 provides a rear profile view of a patient in accordance with an exemplary embodiment of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Figure 2:
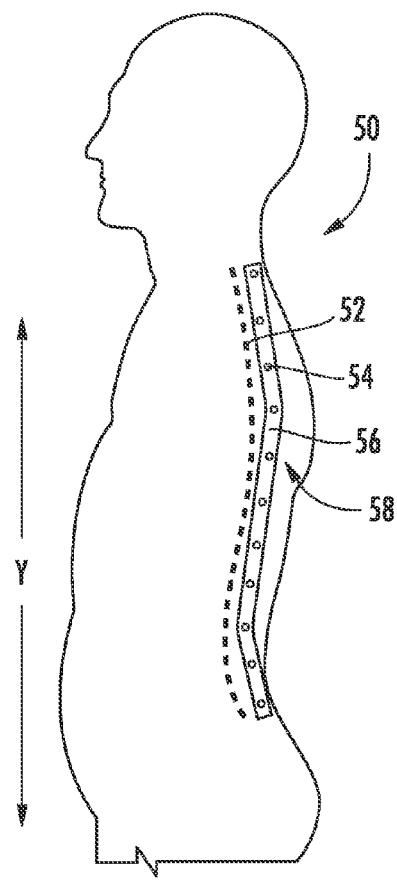
FIG. 2 provides a side profile view of the exemplary patient of FIG. 1.

Referring now to the FIGS., FIG. 1 provides a rear profile view of a patient 50 in accordance with an exemplary embodiment of the present disclosure, and FIG. 2 provides a side profile view of the exemplary patient 50 of FIG. 1. For illustrative purposes, the exemplary patient 50 defines an X direction along an X-axis (FIG. 1), a Y direction along a Y-axis, and a Z direction along a Z-axis (FIG. 2). The X, Y, and Z directions are each mutually perpendicular, defining a three-dimensional coordinate system.

The patient 50 of FIGS. 1 and 2 includes a spine 52, depicted schematically in phantom, defining a shape in an X-Y plane defined by the X and Y axes (FIG. 1), as well as a shape in a Z-Y plane defined by the Z and Y axes (FIG. 2). The three-dimensional shape of the spine 52 of the patient 50 may be a result of, e.g., traumatic injury or a medical condition, such as scoliosis. Regardless, the patient 50 is depicted having undergone a surgical procedure requiring fixation of the spine 52, or more particularly, fixation of a plurality of vertebrae (not shown) of the spine 52. Accordingly, a plurality of pedicle screws 54 are positioned along a length of the spine 52. As used herein, "pedicle screws" refer to a type of spinal instrumentation inserted through a pedicle of the patient's vertebrae and into a body of the vertebrae. More particularly, the plurality of pedicle screws 54 are positioned along a length of the spine 52 in parallel, with a first set 58 spaced from a second set 60 along the X direction. Further, a surgical rod 56 is attached to each respective set 58, 60 of the pedicle screws 54, such that the surgical rods 56 also extend along the length of the spine 52 parallel to one another.

Figure 3:
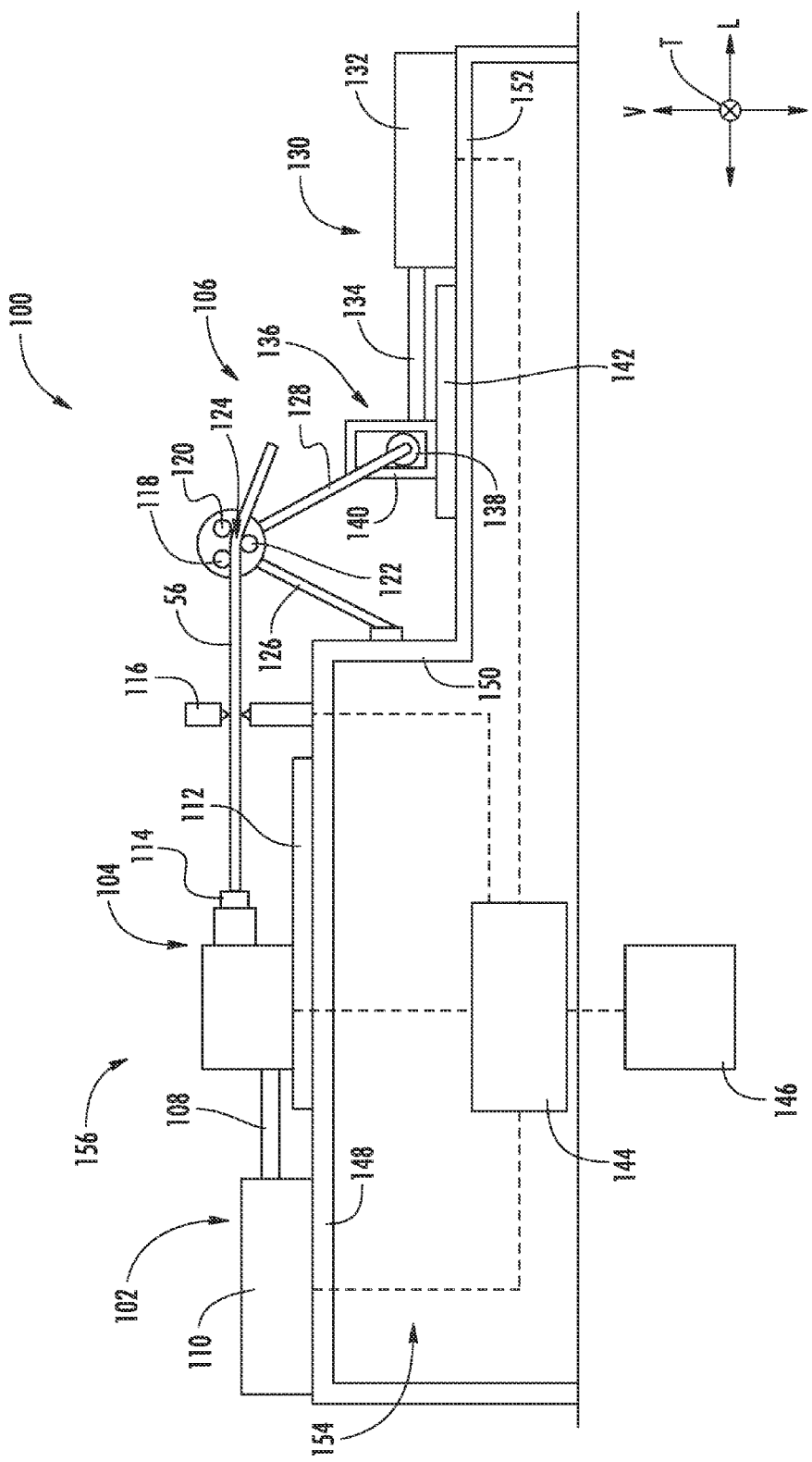
FIG. 3 provides a schematic view of certain aspects of a system in accordance with an exemplary embodiment of the present disclosure.

Referring now to FIG. 3, certain aspects of a system 100 for bending a surgical rod 56 are depicted schematically. The system 100 may bend a surgical rod 56 such that the surgical rod 56 matches a shape of the plurality of screws 54 in, e.g., the spine 52 of the patient 50 (see FIGS. 1 and 2).

The exemplary system 100 defines a vertical direction V, a linear direction L, and a transverse direction, and includes a linear actuator 102, a rotational actuator 104, and a bending mechanism 106. The linear actuator 102 is configured for moving a surgical rod 56 along the linear direction L and the rotational actuator 104 is configured for rotating the surgical rod 56 about the linear direction L. Accordingly, the system 100 may position a surgical rod 56 in the bending mechanism 106 at various locations along a length of the surgical rod 56 and at various rotational orientations. Such a configuration may therefore allow the system 100, or more particularly, the bending mechanism 106, to bend the surgical rod 56 into any desired three-dimensional shape.

More particularly, for the embodiment depicted, the linear actuator 102 defines an arm 108 movable relative to a body 110 along the linear direction L. The linear actuator 102 may be an electric or electro-mechanical actuator, such that the body 110 includes an electric motor (not shown), such as a bipolar stepper motor. However, in other exemplary embodiments, any other suitable linear actuator 102 may be used. For example, in other exemplary embodiments, the linear actuator 102 may be a piezoelectric actuator, a hydraulic actuator, a pneumatic actuator, a linear motor actuator, or any other suitable linear actuator. Further, in certain exemplary embodiments, the linear actuator 102 may be a bidirectional linear actuator wherein the arm 108 may be movable by, e.g., a motor, along the linear direction L away from the body 110 and towards the body 110. Alternatively, however, the linear actuator 102 may instead be a single direction linear actuator, wherein the arm 108 is movable along the linear direction L away from the body 110, but must be manually reset after each use.

Referring still to FIG. 3, the arm 108 of the linear actuator 102 mechanically engages the rotational actuator 104 and the rotational actuator 104 is positioned on a slide assembly 112. Such a configuration may decrease an amount of resistance on the linear actuator 102. Additionally, the rotational actuator 104 is configured for attachment to the surgical rod 56. More particularly, the rotational actuator 104 includes an attachment end 114, which may be configured as an attachment chuck, defining a variably sized opening (not shown) for attaching the rotational actuator 104 to the surgical rod 56. The attachment end 114 may be configured to receive a surgical rod 56 having a diameter of between approximately one millimeter (mm) and approximately ten mm. However, in other embodiments, the attachment end 114 may instead be configured to receive surgical rods 56 having a diameter of between approximately two mm and approximately six mm, or between approximately three mm and approximately five mm. In still other embodiments, however, the attachment end 114 may additionally or alternatively be configured to receive a surgical rod having any other suitable diameter. It should be appreciated that as used herein terms of approximation, such as, "approximately" and "substantially," refer to being within a ten percent margin of error.

The rotational actuator 104 is rotatable approximately three hundred and sixty degrees about the linear direction L relative to the bending mechanism 106. The rotational actuator 104 depicted may be an electric or an electro-mechanical actuator configured for movement between fixed angular positions. For example, the rotational actuator 104 may include a bipolar stepper motor, a servo motor, or any other suitable electric rotational actuator. In other exemplary embodiments, however, the rotational actuator 104 may instead include a fluid powered actuator, such as a hydraulic or pneumatic powered actuator, or any other suitable rotational actuator. Moreover, the rotational actuator 104 may be a single direction actuator or a bidirectional actuator.

Referring still to FIG. 3, the exemplary system 100 of FIG. 3 further includes a cutting tool 116 configured to cut the surgical rod 56 to a desired length, the cutting tool 116 positioned between the linear and rotational actuators 102, 104 and the bending mechanism 106 along the linear direction L. In certain exemplary embodiments, the cutting tool 116 may be a saw using a linear or circular cutting blade, or alternatively may include a jaw with opposing blades (similar to, e.g., a "bolt cutter" configuration).

Moreover, the bending mechanism 106 is positioned downstream of the linear actuator 102, the rotational actuator 104, and the cutting tool 116. More particularly, the bending mechanism 106 is positioned farther along the lateral direction L in a direction in which the surgical rod 56 is moved by the linear actuator 102. The bending mechanism 106 is configured for bending the surgical rod 56 and for the embodiment depicted, the bending mechanism 106 is set up as a "french bender." More particularly, the bending mechanism 106 depicted includes a first upper die 118, a second upper die 120, and a lower die 122. The first upper die 118 and second upper die are 120 spaced from one another along the linear direction L. The lower die 122 is positioned between the first and second upper dies 118, 120 along the linear direction L and is positioned below the first and second upper dies 118, 120 along the vertical direction V. The first and second upper dies 118, 120 and the lower die 122 define a gap 124 along the vertical direction V for receipt of the surgical rod 56. One or more of the dies 118, 120, 122 may be movable along the vertical direction V to vary a size of the gap 124 and bend the surgical rod 56.

For example, in the embodiment depicted, the first upper die 118 may be rigidly connected to a first arm 126, and the second upper die 120 may be rigidly connected to a second arm 128. The lower die 122 may act as a hub connecting the first and second arms 126, 128. Further, the first arm 126 is depicted as being a rigid arm and a second arm 128 is depicted as being a movable arm. Accordingly, the first upper die 118 and the lower die 122 may each be stationary dies, and the second upper die 128 may be a movable die.

A displacement device 130 is further provided with the bending mechanism 106, the displacement device 130 configured to move the second arm 128. More particularly, for the embodiment depicted, the displacement device 130 may be configured as a linear actuator—e.g., configured in a similar manner as the linear actuator 102 described above—including a body 132 and an extension arm 134. The extension arm 134 of the displacement device 130 is attached to the second arm 128 through a vertical slide assembly, which for the embodiment depicted is configured as a roller assembly 136 including a roller 138 slidably positioned within a frame 140. Such a configuration may allow the second arm 128 to pivot about the lower die 122 and about the transverse direction T to move the second upper die 120, change a size of the gap 124, and bend the surgical rod 56. More particularly, for the exemplary embodiment depicted, the surgical rod 56 may be bent a first determined amount at, e.g., a first location, using the bending mechanism 106 by extending the arm 134 of the displacement device 130 away from the body 132 of the displacement device 132. This may cause the second arm 128 to pivot about lower die 122 (and about the transverse direction T), moving the second upper die 120 and closing the gap 124. Once the surgical rod 56 has been bent the first determined amount at the first location, the arm 134 of the displacement device 130 may be retracted towards the body 132 of the displacement device 130 to open the gap 124. This may then allow for the surgical rod 56 to be moved to, e.g., a second location along the lateral direction L, rotated to a second annular orientation about the lateral direction L, and bent a second determined amount at the second location.

The exemplary system 100 additionally includes a horizontal slide assembly 142. The frame 140 of the roller assembly 136 is slidably positioned on the horizontal slide assembly 142.

It should be appreciated, however, that in other exemplary embodiments, any other suitable bending mechanism 106 and/or displacement device 130 may be provided. For example, in other exemplary embodiments, the displacement device 130 may instead be a rotational actuator attached to the second arm 128 at the lower die 122.

Referring still FIG. 3, the exemplary system 100 further includes a controller 144 operably connected to the linear actuator 102, the rotational actuator 104, the bending mechanism 106, and the cutting tool 116. The controller 144 is configured to activate the linear actuator 102, the rotational actuator 104, the bending mechanism 106, and the cutting tool 116 to bend the surgical rod 56 into a desired three-dimensional shape and cut the surgical rod 56 to a desired length. More particularly, the controller 144 is configured to receive information indicative of the desired three-dimensional shape for the surgical rod 56 and activate the linear actuator 102, the rotational actuator 104, and the bending mechanism 106 such that the shape defined by the surgical rod 56 corresponds to the desired three-dimensional shape.

The controller 144 may include a memory and processor, such as a general or special purpose microprocessor operable to execute programming instructions or micro-control code associated with the system 100. The memory may represent random access memory such as DRAM, or read only memory such as ROM or FLASH. In one embodiment, the processor executes programming instructions stored in memory. The memory may be a separate component from the processor or may be included onboard within the processor. Alternative embodiments, however, may include any other suitable configuration.

The system 100 further includes a user interface 146. The exemplary user interface device 146 is depicted schematically as being separate from the controller 144. It should be appreciated, however, that in other exemplary embodiments, the user interface device 146 may instead be integral with the controller 144. One exemplary user interface device 146 may include a touch interface (e.g. a touch screen or touchpad) that allows a user to interact with the user interface device 146 using touch commands. Additionally, or alternatively, the user interface 146 may include a separate display (e.g., monitor) and user input device (e.g., peripherals such as a computer keyboard and/ or mouse). Moreover, the user interface device 146 may allow a user to, e.g., upload information indicative of the desired three-dimensional shape for the surgical rod 56 and initiate bending of a surgical rod 56 using the system 100.

Referring still to FIG. 3, the linear actuator 102, the rotational actuator 104, and the cutting tool 116 are all positioned on a first wall 148 of the system 100. Moreover, the bending mechanism 106 is positioned on a second wall 150 and a third wall 162. More particularly, the stationary arm 126 of the bending mechanism 106 is rigidly attached to the second wall 150 and the displacement device 130 and linear slide assembly 142 of the bending device 106 are positioned on the third wall 152. More particularly, the second arm 128 is attached to the roller assembly 136 which rests on the horizontal slide assembly 142, the horizontal slide assembly 142 positioned on the third wall 152. In certain exemplary embodiments, the first, second, and third walls 148, 150, 152 may be configured as a sterility barrier such that all components above walls 148, 150, and 152 remain sterile. The sterility barrier may therefore prevent germs or other contaminants from passing therethrough and may define a sterile side 154 and a non-sterile side 156. For the exemplary embodiment depicted, the controller 144 is positioned on the sterile side 154 of the sterility barrier. However, in other exemplary embodiments, at least a portion of one or more of the linear actuator 102, the rotational actuator 104, the bending mechanism 106, and the cutting tool 116 may additionally or alternatively be positioned on the sterile side 154 of the sterility barrier. Moreover, in still other exemplary embodiments, rod 56 may be wrapped with a material to assist with maintainin sterility. Such a configuration may allow for the system 100 to be positioned in, e.g., an operating room.

A system 100 for bending a surgical rod 56 in accordance with an exemplary embodiment of the present disclosure may allow for more accurate and time efficient bending the surgical rod 56. More particularly, a system 100 for bending a surgical rod 56 in accordance with the exemplary embodiment may allow a user, such as a surgeon or an assistant acting on behalf of the surgeon, to upload to the exemplary system 100 information indicative of a desired three-dimensional shape for the surgical rod 56 and have the exemplary system 100 automatically bend the surgical rod 56 to the desired three-dimensional shape.

It should be appreciated, however, that the exemplary system 100 of FIG. 3 is provided by way of example only, and that in other exemplary embodiments, the system 100 may have any other suitable configuration. For example, although the exemplary system 100 is depicted in a vertical orientation (e.g., along the vertical direction V), in other exemplary embodiments, the system 100 may not be in a vertical orientation, and instead may be oriented and any other suitable direction. Moreover, in other exemplary embodiments, the exemplary system 100 may include any other suitable organization of the various components. For example, the rotational actuator 104 may be positioned upstream of the linear actuator 102, such that, e.g., the arm 108 of the linear actuator 102 is configured for attachment to the surgical rod 56, and the rotational actuator 104 is configured to rotate the entire linear actuator 102.

Figure 4:
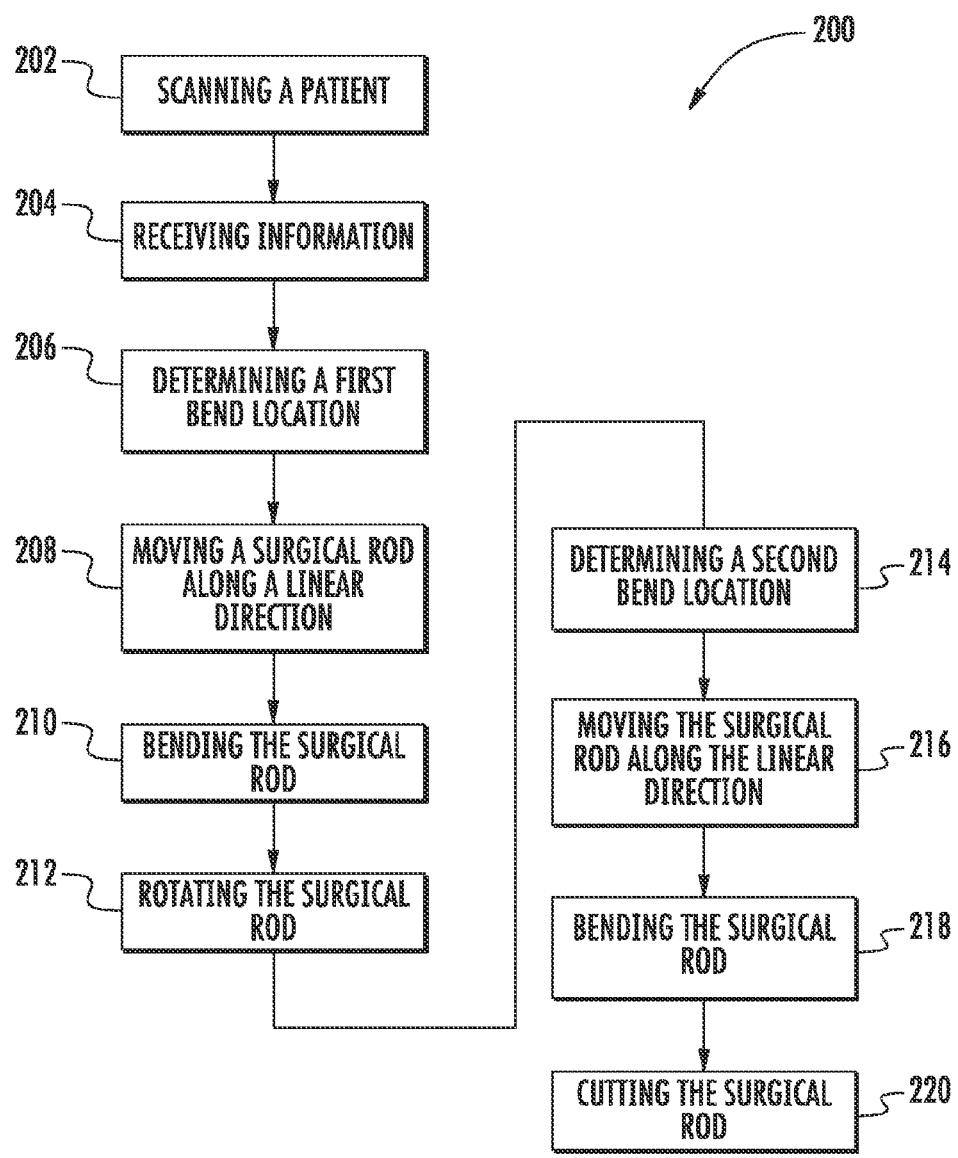
FIG. 4 provides a block diagram of a method in accordance with an exemplary aspect of the present disclosure.

Referring now to FIG. 4, a method (200) for bending a surgical rod in accordance with an exemplary aspect of the present disclosure is provided. In certain exemplary aspects, the method (200) may be used with, e.g., the exemplary system 100 depicted in FIG. 3 and described above.

The exemplary method (200) includes at (202) scanning a patient to determine locations of a plurality of screws positioned in a spine of the patient. The screws may be pedicle screws positioned in various vertebrae of the spine of the patient. Moreover, scanning the patient at (202) may include scanning the patient with a computerized tomography (CT) scanning device or computerized axial tomography (CAT) scanning device. Alternatively, however, any other suitable scanning method or device may be used to determine locations of the plurality of screws positioned in the spine of the patient. For example, in other exemplary embodiments, scanning the patient at (202) to determine locations of the plurality of screws positioned in the spine of the patient may include taking pictures of the exposed plurality of screws positioned in the spine the patient.

The exemplary method (200) additionally includes at (204) receiving with a controller information indicative of a desired shape for the surgical rod. In certain exemplary aspects, the information indicative of the desired shape for the surgical rod received with the controller at (204) may include coordinates of the plurality of screws positioned in the spine of the patient. Such information may be derived from the scan of the patient at (202). For example, the scan of the patient may be analyzed using positioning software to determine the relative position of each of the plurality of screws (e.g., coordinates), and accordingly the desired three-dimensional shape for the surgical rod. It should be appreciated, however, that in other exemplary aspects, receiving information with the controller at (204) may additionally or alternatively include receiving the scan information of the patient and the controller may perform any necessary positioning analysis from the scan to determine, e.g., the relative positions or coordinates of the plurality of screws.

The exemplary method (200) further includes at (206) determining a first bend location of the surgical rod. The first bend location of the surgical rod may be determined at (206) using the information received by the controller at (204) indicative of desired shape for the surgical rod. The exemplary method (200) may additionally include at (208) moving the surgical rod along a linear direction with a linear actuator such that the first bend location of the surgical rod is positioned in a bending mechanism, and at (210) bending the surgical rod at the first bend location a determined amount using the bending mechanism.

In certain exemplary aspects, the method (200) may further include determining an amount to bend the rod. Determining the amount to bend the rod may include determining the coordinates of the pedicle screw at the first bend location, as well as the coordinates of, e.g., the immediately preceding pedicle screw and the immediately subsequent pedicle screw. The amount to bend the rod may be determined based on the relative positions of the three pedicle screws.

Referring still to FIG. 4, the exemplary method (200) further includes at (212) rotating the surgical rod using a rotational actuator after bending the surgical rod at (210) at the first bend location. Such a step may accommodate bending the rod to a desired shape, the desired shape being a three-dimensional shape. Notably, in certain exemplary aspects, rotating the surgical rod at (212) using the rotational actuator may include rotating the surgical rod up to approximately three hundred and sixty degrees.

The exemplary method (200) of FIG. 4 further includes at (214) determining a second bend location of the surgical rod, at (216) moving the surgical rod along the linear direction with the linear actuator such that the second bend location of the surgical rod is positioned in the bending mechanism, and at (218) bending the surgical rod at the second bend location a determined amount using the bending mechanism. Additionally, the exemplary method (200) includes at (220) cutting the surgical rod to a determined length using a cutting tool. In certain exemplary aspects, cutting the surgical rod to the determined length using the cutting tool at (220) may include measuring a length of the surgical rod and determining a desired length of the surgical rod based on the information received at (204).

Moreover, in certain exemplary aspects, moving the surgical rod along the linear direction at (208) or (216) with the linear actuator may further include moving the rotational actuator along the linear direction L. For example, the rotational actuator may be attached to the surgical rod, and the linear actuator may move the entire rotational actuator along with the surgical rod. Further, in still other exemplary aspects of the present disclosure, bending the surgical rod at (210) at the first bend location and/or bending the surgical rod at (218) at the second bend location using the bending mechanism may further include moving a bending die of the bending mechanism relative to two stationary dies of the bending mechanism. In such an exemplary aspect, the bending mechanism may be configured as a french bender, as discussed above with reference to FIG. 3.

It should be appreciated, however, that the method (200) depicted in FIG. 4 is by way of example only, and in other exemplary aspects, the method (200) may include the various elements in any suitable order. For example, in other exemplary aspects, the method (200) may include moving the surgical rod along the linear direction at (216) prior to rotating the surgical rod at (212), or alternatively, the method (200) may include moving the surgical rod along the linear direction at (216) simultaneously with rotating the surgical rod at (212). Moreover, in still other exemplary aspects, the method (200) may not include all the elements depicted in FIG. 4, or alternatively may include additional elements not depicted in FIG. 4. For example, in other exemplary aspects, determining a first bend location at (206) may include determining each bend location, each bend amount, each bend direction, and/or a length of the rod. In such an exemplary aspect, the method (200) may not include, e.g., determining the second bend location at (214) separately from determining the first bend location at (206). Further, in other exemplary aspects, the method (200) may further include additional steps of moving the surgical rod along the linear direction, rotating the surgical rod, and bending the surgical rod, such that the surgical rod defines a shape that corresponds to the position of each of the pedicle screws located by scanning the patient at (202). For example, in other exemplary aspects, the method (200) may include moving, rotating, and bending steps for each pedicle screw location.

Figure 5:
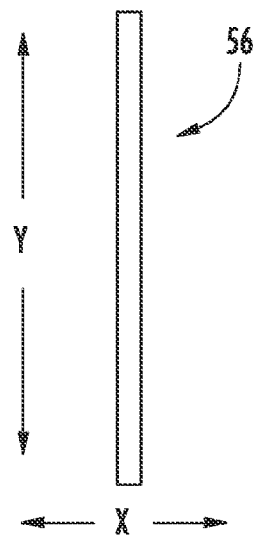
FIG. 5 provides a plan view of a surgical rod in accordance with an exemplary embodiment of the present disclosure in an X-Y plane prior to bending.
Figure 6:
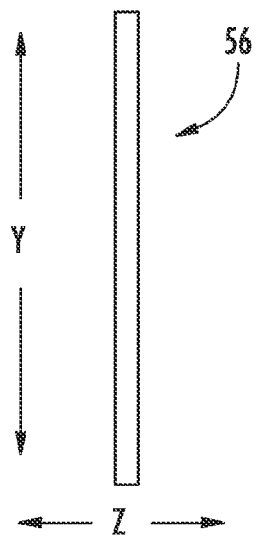
FIG. 6 provides a plan view of the exemplary surgical rod of FIG. 5 in a Y-Z plane prior to bending.
Figure 7:
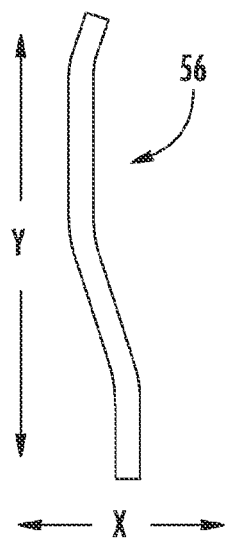
FIG. 7 provides a plan view of the exemplary surgical rod of FIG. 5 in the X-Y plane after bending.
Figure 8:
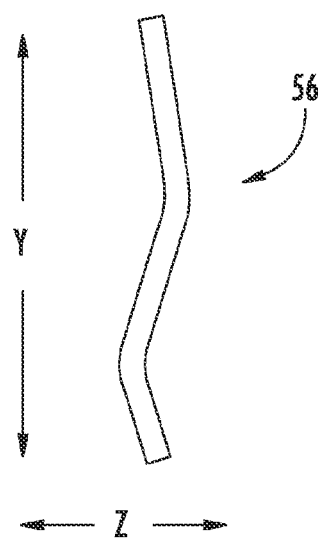
FIG. 8 provides a plan view of the exemplary surgical rod of FIG. 5 in the Y-Z plane after bending.

Referring now to FIGS. 5 through 8, a surgical rod 56 in accordance with an exemplary embodiment of the present disclosure is depicted. In particular, FIG. 5 provides a plan view of a surgical rod 56 in accordance with an exemplary embodiment of the present disclosure in the X-Y plane before bending, and FIG. 6 provides a plan view of the exemplary rod 56 of FIG. 5 in the Y-Z plane before bending. By contrast, FIGS. 7 and 8 provide plan views of the exemplary rod 56 of FIG. 5 in the X-Y plane and in the Y-Z plane, respectively, after bending.

As shown in FIGS. 5 and 6, the exemplary surgical rod 56 may be substantially straight prior to being bent using the exemplary system 100 of FIG. 3 and/or the exemplary method (200) of FIG. 4. By contrast, however, as shown in FIGS. 7 and 8, the exemplary surgical rod 56 may define a shape in the X-Y plane (FIG. 7) and in the Y-Z plane (FIG. 8) that corresponds in shape to the spine 52 of the patient 50 in both the X-Y plane (FIG. 1) and in the Y-Z plane (FIG. 2). More particularly, the exemplary surgical rod 56 may define a three-dimensional shape that corresponds with the position of a plurality of pedicle screws 54 (see FIGS. 1 and 2) positioned in the spine 52 of the exemplary patient 50.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other and examples are intended to be within the scope of the claims if they include structural elements that do not differ from the literal language of the claims, or if they include equivalent structural elements with insubstantial differences from the literal language of the claims.

What is claimed:

1. A system for bending a surgical rod defining a linear direction, the system comprising:
    a linear actuator comprising an arm and configured for moving a surgical rod along the linear direction, wherein the linear actuator further comprises a body, with the arm moveable relative to the body along the linear direction;
    a rotational actuator configured for rotating the surgical rod about the linear direction, the arm of the linear actuator mechanically engaged with the rotational actuator for moving the rotational actuator along the linear direction, the rotational actuator configured for attachment to the surgical rod;
    a bending mechanism configured for bending the surgical rod; and
    a controller operably connected to the linear actuator, the rotational actuator, and the bending mechanism, the controller configured to activate the linear actuator, the rotational actuator, and the bending mechanism to bend the surgical rod into a desired three dimensional shape.

2. The system of claim 1, wherein the bending mechanism is positioned downstream of the linear actuator and the rotational actuator.

3. The system of claim 1, further comprising a cutting tool configured to cut the surgical rod to a desired length.

4. The system of claim 1, wherein the linear direction is a horizontal direction, and wherein the rotational actuator is positioned on a slide assembly and moveable along the slide assembly in the horizontal direction by the linear actuator.

5. The system of claim 1, wherein the rotational actuator defines an opening for attaching to the surgical rod, the opening configured to receive a surgical rod having a diameter of between two (2) millimeters and six (6) millimeters.

6. The system of claim 1, wherein the rotational actuator is rotatable approximately three hundred and sixty degrees about the linear direction relative to bending mechanism.

7. The system of claim 1, wherein the controller is configured to receive information indicative of the desired shape for the surgical rod and to activate the linear actuator, the rotational actuator, and the bending mechanism such that the shape defined by the surgical rod corresponds to the desired shape.

8. The system of claim 1, wherein the bending mechanism includes a first upper die, a second upper die, and a lower die, and wherein the second upper die is pivotable about the lower die to bend the surgical rod.

9. The system of claim 1, further comprising:
    a sterility barrier defining a sterile side and a non-sterile side, wherein at least a portion of one or more of the linear actuators, the rotational actuator, the bending mechanism, and the controller are positioned on the sterile side of the sterility barrier.

* * * * *